United States Patent [19]

Robinson et al.

[11] 4,350,660
[45] Sep. 21, 1982

[54] AMMONIA GAS SENSORS

[75] Inventors: Grenville A. Robinson, Hanwell; Peter N. Kember, Ealing; Derek K. Burns, Wendover, all of England

[73] Assignee: EMI Limited, Hayes, England

[21] Appl. No.: 263,912

[22] Filed: May 13, 1981

[30] Foreign Application Priority Data

Jun. 7, 1980 [GB] United Kingdom ................ 8018738

[51] Int. Cl.$^3$ ............................................ G01N 27/04
[52] U.S. Cl. .................................... 422/90; 23/232 E; 338/34; 422/98
[58] Field of Search .................... 422/90, 94, 96, 97, 422/98; 338/34; 340/633, 634

[56] References Cited

U.S. PATENT DOCUMENTS 3,961,248  6/1976  Kawamara et al. ................ 422/97
3,999,122  12/1976  Winstel et al. ...................... 422/98

OTHER PUBLICATIONS

Merck Index, 9th Ed., p. 325, Copper Phthalocyanine.

Primary Examiner—Michael S. Marcus
Attorney, Agent, or Firm—Fleit & Jacobson

[57] ABSTRACT

An ammonia sensitive element which comprises a body of copper phthalocyanine whose electrical resistance varies with the concentration of ammonia gas to which it is exposed. The body of copper phthalocyanine may be supported on a substrate bearing interlaced electrodes.

4 Claims, 4 Drawing Figures

AMMONIA GAS SENSORS

This invention relates to ammonia gas sensors.

It is frequently necessary when monitoring pollution levels in river water or sewage treatment works, for example, to detect contaminents whose presence is indicated by very small concentrations of ammonia gas. The detection of ammonia gas may also be important in the purification of water intended for public consumption, and an ammonia gas sensor capable of detecting concentrations at least in the range 0 to 100 ppm would be particularly desirable. It is therefore an object of this invention to provide such an ammonia gas sensor.

According to the invention there is provided an ammonia sensitive element which is comprised of a body of copper phthalocyanine whose electrical resistance varies in dependence on the concentration of ammonia gas to which it is exposed.

Figure 1A:
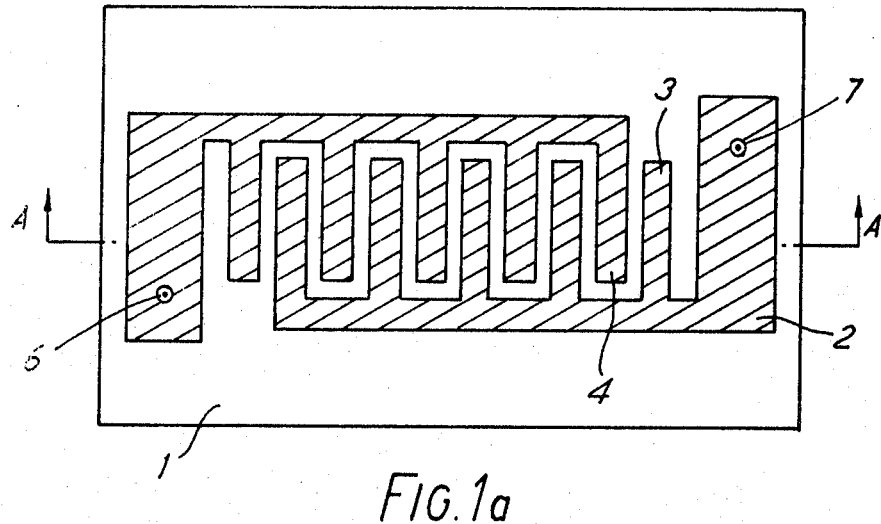
Figure 1B:
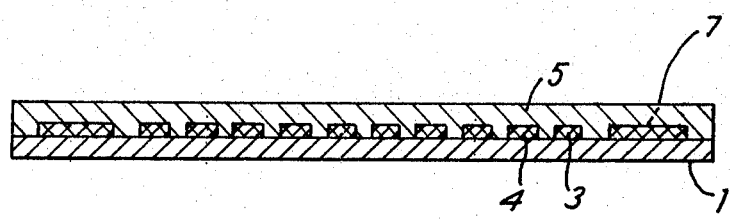
Figure 2:
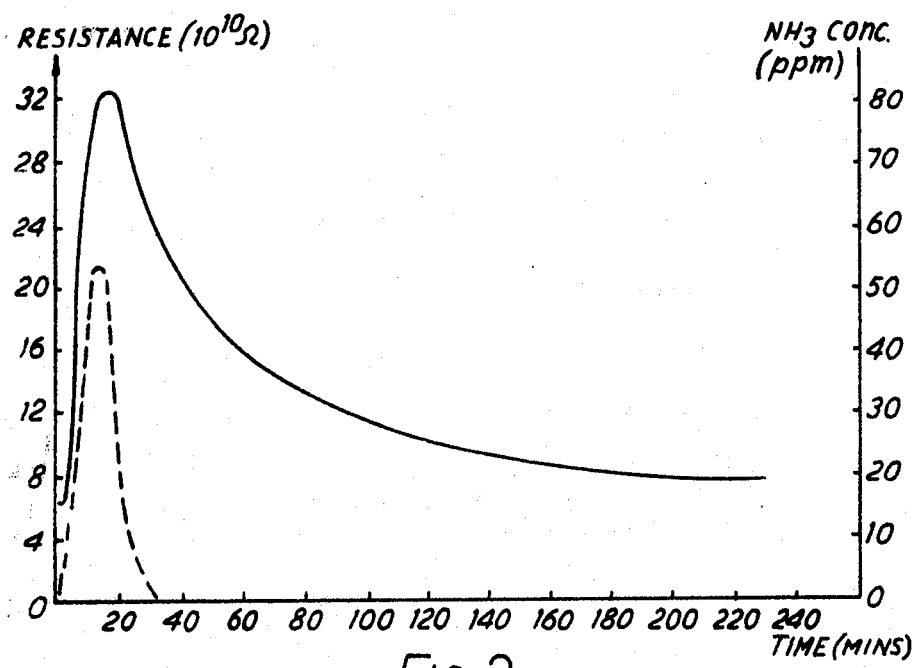
Figure 3:
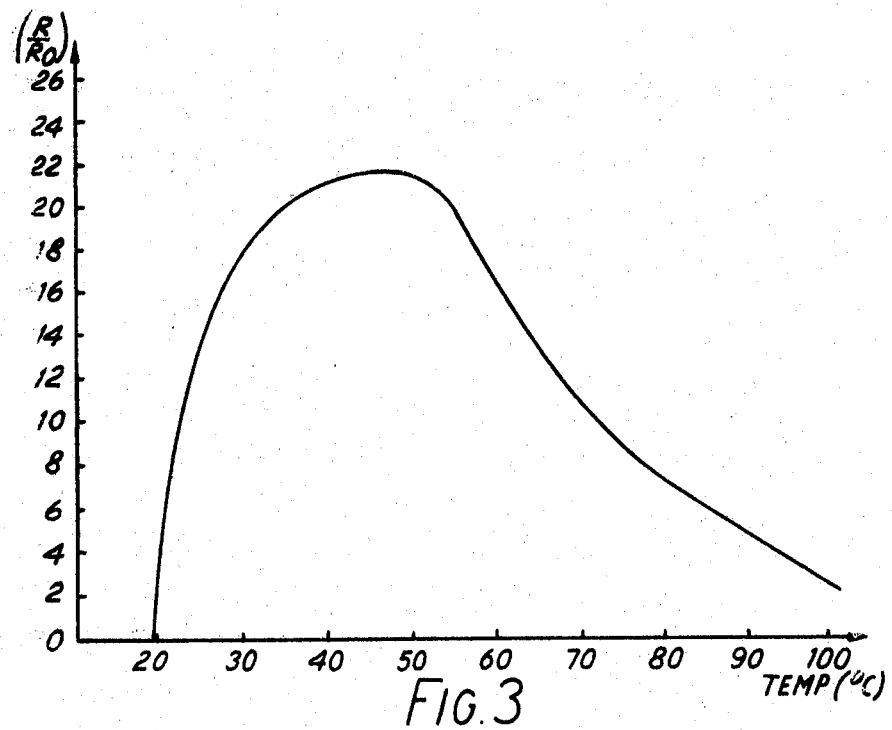

In order that the invention may be more clearly understood and readily carried into effect a specific embodiment thereof, in accordance with the invention, is now described by way of example by reference to the accompanying drawings of which, FIG. 1a shows a plan view of the ammonia sensor and FIG. 1b shows a cross-sectional view along with the line AA and FIGS. 2 and 3 illustrate the response of the element to the concentration of ammonia gas and to temperature respectively.

Referring firstly to FIGS. 1a and 1b, the ammonia sensor comprises a thin glass substrate 1 bearing an evaporated layer 2 of aluminium deposited in the form of interlaced fingers, shown typically at 3 and 4, for example. The fingers, which act as a plurality of electrodes, are typically spaced apart by about 1 mm. A layer of copper phthalocyanine which is shown at 5 in FIG. 1b but which for reasons of clarity is omitted from FIG. 1a, is then deposited onto the plate, to a depth of about 1000 A, so as to cover the electrodes, and lead wires 6 and 7 are secured to the electrodes by means of ultrasonic bonding or alternatively by use of silver paint or silver epoxy. An element constructed in this way is typically about 25 mm long and 5 mm wide, and clearly the layer of copper phthalocyanine may have an alternative thickness, between 100 A and 10,000 A, for example.

In an alternative construction, aluminium electrodes are deposited by photolithographic techniques onto a silicon wafer bearing a thin insulating layer of silicon dioxide. A layer of copper phthalocyanine 1,000 A thick, is then deposited over the electrodes as before. Typically about 40 pairs of electrodes may be deposited on a 2" diameter silicon wafer, the spacing between each pair being about 100 m. The sensor may be used as a multielectrode composite or alternatively the wafer may be divided up to form individual sensors each comprising only a pair of electrodes.

It has been found in practice that copper phthalocyanine sensors are remarkably sensitive to ammonia. FIG. 2 shows a typical result obtained by monitoring the resistance of a copper phthalocyanine sensor when exposed to a small concentration of ammonia gas. These results were obtained by placing the sensor in an air filled, TEFLON (RTM) enclosure into which ammonia gas was admitted. A constant voltage was supplied to the sensor and the current passing therethrough was monitored thereby generating a signal directly proportional to its resistance. The sensor was attached to a PLATFILM (RTM) heater which was used both to heat the sensor and also to monitor its temperature. The concentration of gas introduced into the enclosure was carefully measured using a calibrated infra-red gas analyser. FIG. 2 shows the variation of the sensor resistance with time as a charge of about 50 ppm of ammonia gas in air is introduced into the enclosure. The resistance of the sensor is observed to increase approximately five-fold in response to the introduction of ammonia gas and then to decrease as the gas dissipates.

Surprisingly, the response of a copper phthalocyanine sensor to ammonia gas is found to be markedly greater than a large number of other metal phthayocyanines which have been studied. On exposure to about 110 ppm of ammonia in air, for example, the resistance of a copper phthaloycanine detector is found to increase approximately fifteen-fold. In contrast, when similarly shaped sensors formed of the phthalocyanines of lithium, nickel, vanadium, magnesium, sodium, chloro-aluminium, fluoro-chromium, iron, manganese, aluminium, zinc, cobalt, palladium or lead, or of metal free phthalocyanine or of phthalocyanine green, are exposed to the same concentration of ammonia gas their resistances are found to increase by a factor no greater than 2 and typically less than 1½.

The resistance of the ammonia sensor of this invention is found to vary with temperature, and FIG. 3 shows the variation of the sensor resistance with temperature on exposure to about 110 ppm of ammonia. The resistance is plotted as the ratio of the resistance R of the sensor in the presence of ammonia gas to the resistance R in the absence of ammonia gas. It will be noted that the detector operates at its optimum sensitivity in the temperature range 30° to 65° C. It has also been found that the sensor is least sensitive to changes of humidity at about 55° C. or above.

The present invention, therefore, provides a very convenient ammonia sensitive element which is capable of detecting concentrations as low as 1 ppm, and is particularly suitable for detecting relatively low levels of pollution in river water or sewage treatment works.

What we claim is:

1. A detector sensitive to gaseous ammonia consisting of an electrically insulating support member, an ammonia sensitive layer, consisting solely of copper phthalocyanine, mounted to the support member,
    a plurality of electrodes mounted, in spaced apart relationship, in electrical contact with the layer, the electrical resistance of the layer, as measured between the electrodes, being indicative of ammonia gas sensed by the detector.

2. An ammonia sensitive element according to claim 1 comprising a plurality of interlaced electrodes.

3. An ammonia sensitive element according to claim 1 or claim 2 wherein the electrodes are formed of aluminium.

4. An ammonia sensitive element according to claim 1 or claim 2 wherein the deposit of copper phthalocyanine forms a layer of between 100 and 10,000 Å thick.

* * * * *

UNITED STATES PATENT AND TRADEMARK OFFICE
CERTIFICATE OF CORRECTION

PATENT NO. : 4,350,660
DATED : September 21, 1982
INVENTOR(S) : Grenville A. ROBINSON, et al It is certified that error appears in the above-identified patent and that said Letters Patent are hereby corrected as shown below:

On the title page,

[22] Filed: change "May 13, 1981"

to --May 15, 1981--

Signed and Sealed this

Eleventh Day of January 1983

[SEAL]

Attest:

GERALD J. MOSSINGHOFF

Attesting Officer

Commissioner of Patents and Trademarks

Disclaimer and Dedication 4,350,660.—*Grenville A. Robinson*, Hanwell, *Peter N. Kember*, Ealing, and *Derek K. Burns*, Wendover, England. AMMONIA GAS SENSORS. Patent dated Sept. 21, 1982. Disclaimer and Dedication filed Nov. 1, 1983, by the assignee, *Emi Ltd.*

Hereby disclaims and dedicates to the Public the entire remaining term of said patent.

[*Official Gazette December 11, 1984.*]